United States Patent [19]

Kaplan et al.

[11] Patent Number: 4,478,851
[45] Date of Patent: * Oct. 23, 1984

[54] BENZYLIDENE DERIVATIVES AND COMPOSITIONS CONTAINING THEM

[75] Inventors: Jean-Pierre Kaplan, Chevilly Larue; Bernard Raizon, Vigneux, both of France

[73] Assignee: Synthelabo, Paris, France

[*] Notice: The portion of the term of this patent subsequent to Aug. 23, 2000 has been disclaimed.

[21] Appl. No.: 490,478

[22] Filed: May 2, 1983

Related U.S. Application Data

[62] Division of Ser. No. 233,404, Feb., 1981, Pat. No. 4,400,536.

[30] Foreign Application Priority Data

Feb. 12, 1980 [FR] France ................. 80 03009

[51] Int. Cl.³ .................. A61K 31/135; C07C 119/14
[52] U.S. Cl. ..................................... 424/330; 564/269
[58] Field of Search ........................ 564/269; 424/330

[56] References Cited

U.S. PATENT DOCUMENTS 4,400,536  8/1983  Kaplan et al. ................ 564/269

Primary Examiner—Natalie Trousof
Assistant Examiner—Leah Hendriksen
Attorney, Agent, or Firm—Wegner & Bretschneider

[57] ABSTRACT

Benzylidene derivatives of the formula:

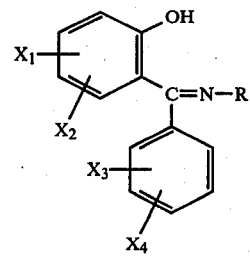

in which each of $X_1$, $X_2$, $X_3$ and $X_4$ independently of one another represents hydrogen, halogen, a linear or branched alkyl radical of 1 to 4 carbon atoms, $CF_3$, $NO_2$, phenyl, methoxy, or amino, at least two of the substituents $X_1$, $X_2$, $X_3$ and $X_4$ being different from hydrogen, and R represents a linear or branched alkyl radical of 1 to 16 carbon atoms or an alkenyl radical of 2 to 8 carbon atoms, which may be produced by reaction of the corresponding ketones with an amine, are active on the central nervous system, especially as anticonvulsants.

6 Claims, No Drawings

BENZYLIDENE DERIVATIVES AND COMPOSITIONS CONTAINING THEM

This application is a divisional of United States application Ser. No. 233,404, filed Feb. 11, 1981 now U.S. Pat. No. 4,400,536.

DESCRIPTION

The present invention relates to benzylidene derivatives, their preparation and pharmaceutical compositions containing them.

Various benzylidene derivatives are described in our U.S. Pat. No. 4,094,992 and patent application Ser. No. 107,512 of December 27, 1979.

The compounds of the present invention have the formula

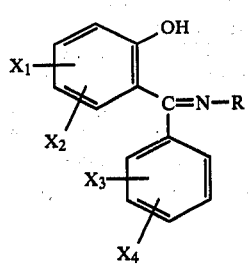

(I)

in which each of $X_1$, $X_2$, $X_3$ and $X_4$ independently of one another represents hydrogen, halogen, a linear or branched alkyl radical of 1 to 4 carbon atoms, $CF_3$, $NO_2$, phenyl, methoxy or amino ($-NH_2$), at least two of the substituents $X_1$, $X_2$, $X_3$ and $X_4$ being different from hydrogen, and R represents a linear or branched alkyl radical of 1 to 16 carbon atoms or an alkenyl radical of 2 to 8 carbon atoms.

The preferred compounds of the invention are those in which R is an alkyl radical of 1 to 8 carbon atoms, and more particularly the compounds in which R is an alkyl having 3, 4, 5 or 6 carbon atoms or an alkenyl having 3, 4, 5 to 6 carbon atoms.

Amongst these compounds, the preferred compounds are those in which each of the radicals $X_1$, $X_2$, $X_3$ and $X_4$ independently of one another is hydrogen, halogen, or methyl, and more particularly those in which $X_2=H$, $X_1$ is in the 4-position, and $X_3$ and $X_4$ are in the 2'- and 4'-positions.

According to a feature of the invention, the compounds of formula (I) are prepared in accordance with the following equation:

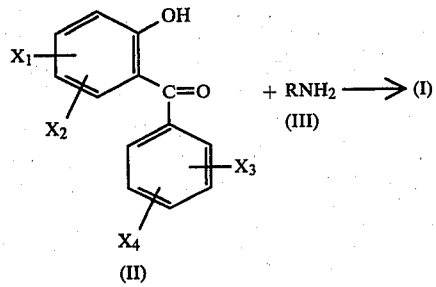

The compounds of formula (II) are described in our previous patents mentioned above.

The compounds of formula (III) are used in the form of the base or the hydrochloride and are described in the literature.

The reaction may be carried out in an alcoholic solvent, such as methanol or ethanol, at a temperature from 10° C. to the boiling point of the solvent, in the presence of an alkali metal or alkali metal alcoholate.

The following Examples illustrate the invention. The IR and NMR spectra confirmed the structure of the compounds.

EXAMPLE 1.

[n-Butylimino-(2-chlorophenyl)-methyl]-4-chlorophenol.

[$X_1=$4-Cl, $X_2=$H, $X_3=$2-Cl, $X_4=$H, R=n-$C_4H_9$]

1.

5-Chloro-2-hydroxyphenyl-(2-chlorophenyl)-methanone.

A mixture of ortho-chlorobenzoic acid (313.14 g), thionyl chloride (600 ml) and 0.5 ml of pyridine is heated at the reflux temperature for 6 hours. The excess thionyl chloride is subsequently evaporated and two 250 ml portions of benzene are then added and evaporated each time. This yields ortho-chlorobenzoyl chloride.

257.12 g of p-chlorophenol, 2 liters of methylene chloride and 280 ml of triethylamine are introduced into a 10 liter reactor. The o-chlorobenzoyl chloride obtained above, dissolved in 1 liter of methylene chloride, is introduced in the course of 2 hours. The reaction mixture is heated at the reflux temperature for 12 hours and is then left to stand for 48 hours. 3 liters of water are then added, the mixture is stirred for 10 minutes and the organic phase is decanted, washed with water, and dried over $MgSO_4$. The mixture is filtered and the filtrate is evaporated to dryness. This yields an oil which is dissolved in 1 liter of petroleum ether, and the solution is cooled. The ester of formula

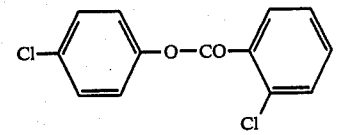

crystallises out. It is filtered off, drained and dried at 50° C.

250 g of this ester are heated with 250 g of aluminium chloride. After hydrolysis of the product, the compound of formula (II) obtained is extracted with chloroform. The extract is dried over $MgSO_4$ and filtered and the filtrate is evaporated to dryness. After recrystallisation of the residue from petroleum ether, draining and drying in a desiccator, the ketone obtained melts at 107.9° C.

2.

2-[Butylimino-(2-chlorophenyl)-methyl]-4-chlorophenol.

7 g of the ketone obtained above, dissolved in 200 ml of ethanol, are introduced into a 500 ml round-bottomed flask and two 25 ml portions of n-butylamine are added. The mixture is stirred until the ketone has completely disappeared. The solution is then evaporated to dryness and the residue is taken up in chloroform. The chloroform phase is washed with water (several times), left to separate out and dried over MgSO$_4$. The mixture is filtered on a glass frit filter and the filtrate is then evaporated to dryness. The product is crystallised from petroleum ether and the precipitate is carried onto a frit, drained and dried in a desiccator. The compound obtained melts at 49.6° C.

In another experiment, a compound melting at 57.2° C. (according to the method of differential thermal analysis) is obtained in the same yield. The product is the same and there are therefore probably two different crystalline forms.

EXAMPLE 2

2-[n-Butylimino-(2,4-dimethylphenyl)-methyl]-4-methylphenol.

[X$_1$=4-CH$_3$, X$_2$=H, X$_3$=2-CH$_3$, X$_4$=4-CH$_3$, R=n-C$_4$H$_9$]

2-Hydroxy-5-methylphenyl-(2,4-dimethylphenyl)-methanone (obtained in accordance with one of the processes described in our patents mentioned above) is used in accordance with the following reaction scheme:

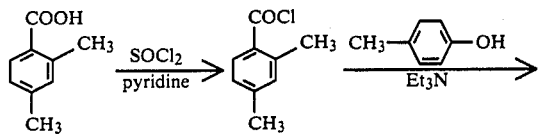

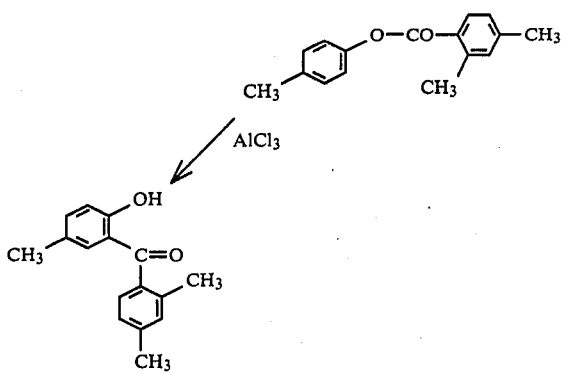

6.25 g of the ketone, dissolved in 200 ml of methanol, are introduced into a 500 ml round-bottomed flask. 75 ml of n-butylamine are added and the reaction described in Example 1 is carried out. The compound is obtained in the form of an oil.

The compounds of the invention which have been prepared by way of examples are summarised in the Table below. The refractive indices n$_D^{23}$ are given for the compounds which are in the form of an oil.

TABLE

| Compound | X$_1$ | X$_2$ | X$_3$ | X$_4$ | R | Melting point (°C.) or refractive index |
|---|---|---|---|---|---|---|
| 1 | 4-Cl | H | 2-Cl | H | CH$_3$ | 127.2 |
| 2 | 4-Cl | H | 2-Cl | H | n-C$_4$H$_9$ | 49.6 or 57.2 |
| 3 | 4-Cl | H | 2-Cl | H | C$_2$H$_5$ | 69.2 |
| 4 | 4-Cl | H | 2-Cl | H | n-C$_3$H$_7$ | 58.9 |
| 5 | 4-Cl | H | 2-Cl | H | n-C$_5$H$_{11}$ | 61.4 |
| 6 | 4-Cl | H | 2-Cl | H | n-C$_6$H$_{13}$ | n$_D^{23}$ = 1.5831 |
| 7 | 4-Cl | H | 2-Cl | H | i-C$_5$H$_{11}$ | 46.8 |
| 8 | 4-Cl | H | 2-Cl | H | n-C$_7$H$_{15}$ | 65.3 |
| 9 | 4-Cl | H | 2-Cl | H | CH(CH$_3$)CH$_2$CH(CH$_3$)CH(CH$_3$)CH$_3$ (branched) | 93.7 |
| 10 | 4-Cl | H | 2-Cl | H | C$_8$H$_{17}$ | n$_D^{23}$ = 1.5723 |
| 11 | 4-Cl | H | 2-Cl | H | C$_9$H$_{19}$ | n$_D^{23}$ = 1.5662 |
| 12 | 4-Cl | H | 2-Cl | H | C$_{10}$H$_{21}$ | n$_D^{23}$ = 1.5622 |
| 13 | 4-Cl | H | 2-Cl | H | C$_{11}$H$_{23}$ | n$_D^{23}$ = 1.5584 |
| 14 | 4-Cl | H | 2-Cl | H | C$_{12}$H$_{25}$ | n$_D^{23}$ = 1.5547 |
| 15 | 4-Cl | H | 2-Cl | H | C$_{13}$H$_{27}$ | n$_D^{23}$ = 1.5513 |
| 16 | 4-Cl | H | 2-Cl | H | C$_{14}$H$_{29}$ | F∼30 |
| 17 | 4-Cl | H | 2-Cl | H | C$_{15}$H$_{31}$ | 41.6 |
| 18 | 4-Cl | H | 2-Cl | H | C$_{16}$H$_{33}$ | n$_D^{23}$ = 1.5432 |
| 19 | 4-Cl | H | 2-Br | H | n-C$_4$H$_9$ | 70.5 |
| 20 | 4-CH$_3$ | H | 2-CH$_3$ | H | n-C$_4$H$_9$ | n$_D^{23}$ = 1.5776 |
| 21 | 4-CH$_3$ | H | 2-CH$_3$ | 4-CH$_3$ | n-C$_4$H$_9$ | n$_D^{23}$ = 1.5762 |
| 22 | 4-CH$_3$ | H | 2-CH$_3$ | 5-CH$_3$ | n-C$_4$H$_9$ | 63.8 |
| 23 | 6-CH$_3$ | 4-CH$_3$ | 2-CH$_3$ | 4-CH$_3$ | n-C$_4$H$_9$ | n$_D^{23}$ = 1.5750 |
| 24 | 4-Cl | H | 2-Cl | H | CH(C$_3$H$_7$)CH$_3$ | 75.1 |

TABLE-continued

| Compound | X₁ | X₂ | X₃ | X₄ | R | Melting point (°C.) or refractive index |
|---|---|---|---|---|---|---|
| 25 | 4-Cl | H | 2-Cl | H | (CH₃)CH—CH₂—CH(CH₃)₂ | 70.6 |
| 26 | 4-Cl | H | 2-Cl | H | (CH₂)₂C(CH₃)₃ | 95 |
| 27 | 4-Cl | H | 2-Cl | H | CH(C₂H₅)₂ | 139.5 |
| 28 | 4-Cl | H | 2-Cl | H | CH₂—CH=CH₂ | 81.1 |
| 29 | 4-Cl | H | 2-Cl | H | (CH₃)CH—CH(CH₃)—CH₃ | 120.7 |
| 30 | 4-Cl | H | 2-Cl | H | CH=CH—CH₃ | 90.6 |
| 31 | 4-Cl | H | 2-Cl | H | CH₂—CH(C₃H₇)₂ | $n_D^{23} = 1.5733$ |
| 32 | 6-CH₃ | 4-CH₃ | 2-Br | H | n-C₄H₉ | $n_D^{23} = 1.5968$ |
| 33 | H | H | 2-NH₂ | 5-Cl | n-C₄H₉ | 61 |
| 34 | 4-Br | H | 2-Br | H | n-C₄H₉ | 75.6 |
| 35 | 4-F | H | 4-CF₃ | H | n-C₄H₉ | 62.6 |
| 36 | t.-4-C₄H₉ | H | 4-Cl | H | n-C₄H₉ | 90.1 |
| 37 | 4-F | H | 4-Cl | H | n-C₄H₉ | 61.6 |
| 38 | 4-CF₃ | H | 4-F | H | n-C₄H₉ | 55.6 |
| 39 | 4-C₆H₅ | H | 4-Cl | H | n-C₄H₉ | 127.6 |
| 40 | 4-Br | H | 2-Cl | H | n-C₄H₉ | 37.7 |
| 41 | 4-F | H | 2-Cl | 5-Cl | n-C₄H₉ | 78 |
| 42 | 4-F | H | 3-Cl | 4-Cl | n-C₄H₉ | 117.1 |
| 43 | 4-Cl | H | 2-Cl | H | CH₂—CH(CH₃)₂ | 56.1 |
| 44 | 4-Cl | H | 2-Cl | H | CH₂-cyclopropyl | 75.3 |
| 45 | 4-Cl | H | 2-Cl | H | CH₂—CH(CH₃)(CH₂—CH₃) | 29.5 |
| 46 | 4-Br | H | 2-F | H | n-C₄H₉ | $n_D^{22} = 1.5952$ |
| 47 | 4-Cl | H | 2-Cl | H | CH₂-cyclobutyl | 101.8 |
| 48 | 4-F | H | 2-Cl | H | n-C₄H₉ | $n_D^{23} = 1.5773$ |
| 49 | 4-F | H | 2-Cl | H | n-C₅H₁₁ | 43.7 |
| 50 | 4-Cl | H | 4-Cl | H | n-C₄H₉ | $n_D^{20} = 1.5889$ |
| 51 | 4-Cl | H | 2-F | H | n-C₅H₁₁ | 30–31 |
| 52 | 4-Cl | H | 2-F | H | n-C₄H₉ | 37.5 |
| 53 | 4-Cl | H | 2-Cl | H | CH₂—CH₂—CH=CH₂ | 67–68 |
| 54 | 4-Cl | H | 2-Cl | H | CH₂—CH=CH—CH₃ | $n_D^{19} = 1.6140$ |
| 55 | 4-Cl | H | 2-Cl | H | CH₂—C(CH₃)=CH₂ | 47–48 |

The compounds of the invention have been subjected to pharmacological tests demonstrating their action on the central nervous system.

The acute toxicity was determined on mice by intraperitoneal administration. The LD 50 (50% lethal dose), which causes death in 50% of the animals, is more than 1,000 mg/kg.

The action of the compounds was demonstrated by their antagonism towards the mortality caused in mice by bicuculline. Bicuculline is a relatively selective blocker of post-synaptic GABA-ergic receptors and its convulsive and lethal effects are antagonised by compounds which raise the level of cerebral GABA or which possess a GABA-mimetic action. The 50% active dose (AD 50) of the substances studied, namely the dose which protects 50% of the animals against the effect of bicuculline, was evaluated.

The AD 50 of the compounds of the invention varies from 20 to 80 mg/kg, administered intraperitoneally.

The compounds of the invention are active as anticonvulsives. They can be used in human and veterinary therapy for the treatment of various diseases of the central nervous system, for example for the treatment of psychoses and of certain neurological diseases, such as epilepsy.

The invention consequently includes pharmaceutical compositions comprising a compound of formula (I) as active principle, in association with any pharmaceutical excipient suitable for their administration, in particular oral administration (tablets, coated tablets, sugar-coated pills, capsules, cachets, or solutions or suspensions to be taken orally) or parenteral administration.

The daily dosage can range from 100 to 1,500 mg.

We claim:

1. A compound of the formula

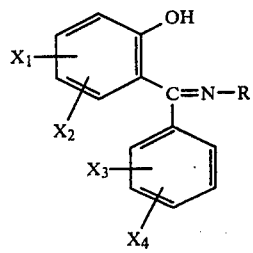

wherein R represents a linear or branched alkyl radical of 1 to 16 carbon atoms or an alkenyl radical of 2 to 8 carbon atoms, wherein $X_1$, $X_2$ and $X_4$ independently of one another represent hydrogen, halogen or methyl at least one substituent $X_1$, $X_2$ and $X_4$ being different from hydrogen, and $X_3$ represents halogen or methyl.

2. A compound according to claim 1, in which R is an alkyl radical of 1 to 8 carbon atoms.

3. A compound according to claim 1, in which R is an alkyl or alkenyl radical of 3, 4, 5 or 6 carbon atoms.

4. A compound according to claim 1, in which $X_2$ is H, $X_1$ is in the 4-position, and $X_3$ and $X_4$ are in the 2'- and 4'-positions.

5. An anti-convulsant pharmaceutical composition comprising an effective anti-convulsant amount of a compound as claimed in claim 1 in association with a suitable pharmaceutical excipient.

6. A method for providing an anti-convulsant effect to a patient which comprises administering to said patient an effective amount of a compound of claim 1.

* * * * *